United States Patent [19]

Cunningham et al.

[11] Patent Number: 4,896,671
[45] Date of Patent: Jan. 30, 1990

[54] CATHETER WITH CONTOURED ABLATION ELECTRODE

[75] Inventors: A. David Cunningham, London, England; Paul M. Leah, Schroon Lake; Harvey W. Collins, Gansevoort, both of N.Y.

[73] Assignee: C. R. Bard, Inc., Murray Hill, N.J.

[21] Appl. No.: 226,780

[22] Filed: Aug. 1, 1988

[51] Int. Cl.[4] ........................... A61B 5/04; A61N 1/05
[52] U.S. Cl. ..................................... 128/642; 128/786; 606/39
[58] Field of Search ................. 128/642, 784–786, 128/419 P, 419 S, 303.13

[56] References Cited

U.S. PATENT DOCUMENTS

| | | | |
|---|---|---|---|
| 1,932,258 | 10/1933 | Wappler | 174/89 |
| 3,757,789 | 9/1973 | Shanker | 128/404 |
| 4,248,237 | 2/1981 | Kenny | 128/419 P |
| 4,289,138 | 9/1981 | Halvorsen | 128/642 |
| 4,357,947 | 11/1982 | Littleford | 128/786 |
| 4,419,819 | 12/1983 | Dickhudt et al. | 29/857 |
| 4,432,377 | 2/1984 | Dickhudt | 128/786 |
| 4,437,474 | 3/1984 | Peers-Travarton | 128/784 |
| 4,552,157 | 11/1985 | Littleford | 128/786 |
| 4,553,534 | 11/1985 | Lemole | 128/784 |
| 4,614,192 | 9/1986 | Imran et al. | 128/419 D |
| 4,641,649 | 2/1987 | Walinsky et al. | 128/303.1 |
| 4,660,571 | 4/1987 | Hess et al. | 128/784 |
| 4,679,572 | 7/1987 | Baker, Jr. | 128/786 |

FOREIGN PATENT DOCUMENTS

2721775 11/1978 Fed. Rep. of Germany ... 128/419 P

OTHER PUBLICATIONS

Ewy et al., "Electrode System . . . Electrodes", Med. Inst., vol. 12, No. 5, Sep.–Oct. 1978, pp. 296–300.
Tripolar His–Bundle Electrode, U.S. Catheter & Inst. Corp., 10/1971.
Onkar S. Narula et al., Am. J. Cardiology, Jul. 1984, pp. 186–192.
J. Gallagher et al., N.E. J. Medicine, vol. 306, No. 4, Jan. 28, 1982, pp. 194–200.
Melvin M. Scheinman, JAMA, vol. 248, No. 7, Aug. 20, 1982, pp. 851–855.
R. Gonzalez et al., Am. J. Physiol, 241, (Heart Circ. Physiol., 10), H283–H287, 1981.

*Primary Examiner*—Lee S. Cohen
*Attorney, Agent, or Firm*—Wolf, Greenfield & Sacks

[57] ABSTRACT

A catheter which can be advanced through a body vessel to an internal organ, typically the heart, for electroshock ablation. The catheter includes a catheter lead and a contoured electroshock ablation electrode attached to the catheter lead at or near its distal end. The contoured electrode and the catheter lead are configured to provide a high arcing threshold. The electrode has a smoothly curved surface free of sharp edges. The catheter lead at the junction with the electrode has a smaller diameter than the electrode. Preferably, the diameter of the catheter lead at the junction with the electrode is no more than one third the diameter of the electrode. The catheter lead includes a flexible sheath that is tapered to a smaller diameter at or near the junction of the electrode with the catheter lead. In a preferred embodiment, the electrode includes a cylindrical surface coaxial with the catheter lead and hemispherical end surfaces having the same diameter as the cylindrical surface. The catheter permits delivery of high energy shocks without arcing.

35 Claims, 3 Drawing Sheets

Fig. 9A
ARCING THRESHOLD- -VOLTS
CATHODAL ANODAL

Fig. 9B
ARCING THRESHOLD- AMPS
CATHODAL ANODAL

Fig. 9C
ARCING THRESHOLD- JOULES
CATHODAL ANODAL

CATHETER WITH CONTOURED ABLATION ELECTRODE

FIELD OF THE INVENTION

This invention relates to electroshock ablation catheters and, more particularly, to a catheter having at or near its distal end an electroshock ablation electrode that is contoured to provide a high arcing threshold. The catheter is advanced through a blood vessel into the heart and is used for ablation of tissue within the heart.

BACKGROUND OF THE INVENTION

In the treatment of heart malfunctions, cutting, or ablation, of specific conduction paths in the region of the A-V node, the His bundle, or the ventricles has been found beneficial. This can be accomplished surgically, but recently more preferable, nonsurgical techniques have been developed.

In one prior art technique, a catheter having an optical fiber passing through it is advanced to the desired location in the heart. Energy from an external laser is conducted by the optical fiber into the heart. This technique is described by Onkar S. Narula et al in "Microtransection of the His Bundle With Laser Radiation Through a Pervenous Catheter: Correlation of Histologic and Electrophysiologic Data," *Am. J. Cardiology,* July, 1984, pp. 186–192. The equipment necessary for laser ablation is relatively expensive, and the optical fiber is somewhat difficult to maneuver to the desired location.

A technique for high frequency ablation of the His bundle in the heart is disclosed in U.S. Pat. No. 4,641,649 issued Feb. 10, 1987 to Walinsky et al. A catheter in the form of a coaxial transmission line with an antenna at its distal end is advanced into the heart in the region of the His bundle, and the potentials sensed by the catheter are measured and displayed. The catheter position is adjusted until the desired potentials are obtained. Then, high frequency energy is applied to the transmission line, causing ablation of portions of the His bundle. The high frequency technique may produce undesirable charring of tissue surrounding the antenna.

In an electroshock ablation technique, a catheter provided with one or more electrodes is advanced through a blood vessel into the heart, and a plate-like electrode is positioned on the patient's skin. A high energy electrical pulse is applied between the electrodes, causing a modification of the conduction system by ablation. Such a technique is described by J. Gallagher et al in "Catheter Technique for Closed Chest Ablation of the Atrioventricular Conduction System," *N. E. J. Medicine,* Vol. 306, No. 4, Jan. 28, 1982, pp. 194–200 and by Melvin M. Scheinman et al in Catheter-Induced Ablation of the Atrioventricular Junction to Control Refractory Supraventricular Arrhythmias," *JAMA,* Vol. 248, No. 7, Aug. 20, 1982, pp. 851-855. A voltage on the order of 2,000 volts is applied for a time on the order of a few milliseconds.

One problem associated with prior practice of the electroshock ablation technique has been that arcing often occurs in the region of the electrode. Such arcing can cause undesired burning of tissue and produces shock waves which can further damage the surrounding tissue. The arcing occurs across bubbles which form at the surface of the electrode when it is energized. It is desirable to minimize arcing and the resulting shock waves.

In the past, electroshock ablation has been performed with conventional pacing catheters which include ring electrodes and distal electrodes that are similar to ring electrodes but have a rounded tip. When these electrodes are used for electroshock ablation, arcing often occurs. A variety of other electrode shapes have been disclosed for pacing applications. In pacing applications, the applied voltage is on the order of a few volts, and arcing is not a factor.

PCT Publication No. WO 80/02231 published Oct. 30, 1980, relates to an electrode lead for pacemakers wherein a conductive electrode tip has a spherical portion and a cylindrical portion attached to the distal end of the catheter. The cylindrical portion is tapered to a smaller diameter at the intersection with the spherical portion. The cylindrical portion is not insulated.

U.S. Pat. No. 3,757,789 issued Sept. 11, 1973 to Shanker relates to an electrode for use in a body organ stimulator such as a cardiac pacer. The electrode system includes a spherical electrode tip with electrical connection made by a cylindrical pin of smaller diameter than the sphere. The catheter tube is tapered to a smaller diameter at the intersection with the spherical electrode tip.

U.S. Pat. No. 1,932,258 issued Oct. 24, 1933 to Wappler discloses a surgical electrode for transmission of high frequency electrical energy to body tissue. The electrode includes a flat, blade-like arm which produces a cutting spark when brought into contact with tissue and a spherical arm which is used for coagulation in a nonsparking manner.

U.S. Pat. No. 4,660,571 issued Apr. 28, 1987 to Hess et al discloses a percutaneous lead with a hemispherical distal electrode and a ring electrode. The lead is suitable for use in mapping, ablation and pacing.

It is a general object of the present invention to provide improved apparatus for nonsurgical electroshock ablation of desired portions of internal body organs.

It is another object of the present invention to provide improved apparatus for electroshock ablation of tissue within the heart.

It is a further object of the present invention to provide an electroshock ablation catheter with a contoured electrode that provides a high arcing threshold.

It is yet another object of the present invention to provide an electroshock ablation catheter having at or near its distal end a contoured electrode that permits application of high voltage, high current pulses to tissue without arcing.

SUMMARY OF THE INVENTION

According to the present invention, these and other objects and advantages are achieved in a catheter which can be advanced through a body vessel to an internal organ for electroshock ablation of a desired portion of the internal organ. The catheter includes a catheter lead and a contoured electroshock ablation electrode attached to the catheter lead at or near its distal end. The catheter lead includes an insulated conductor coupled to the contoured electrode. Electrical energy is supplied from an external source through the insulated conductor to the contoured electrode for ablation of a desired portion of the internal organ.

The contoured electrode and the catheter lead are configured to provide a high arcing threshold. The electrode has a smoothly curved surface free of sharp edges. The catheter lead at the junction with the electrode has a smaller diameter than the electrode. The electrode surface curves inwardly at its proximal end to meet the catheter lead. Preferably, the diameter of the catheter lead at the junction with the electrode is no more than one third the diameter of the electrode. As a result, high energy ablation shocks can be delivered without arcing.

In a preferred embodiment, the smoothly curved surface of the electrode includes a cylindrical surface coaxial with the catheter lead and a proximal end surface that is typically hemispherical joining the cylindrical surface to the catheter lead. The distal end surface of the electrode is preferably hemispherical.

The catheter typically includes a flexible, insulating sheath surrounding a major portion of the insulated conductor. The insulating sheath preferably has a diameter approximately equal to the maximum cross-sectional dimension of the electrode and is tapered in a region close to the electrode from full diameter at a first point on the catheter axis to the diameter of the insulated conductor at a second point on the catheter axis. In one embodiment, the sheath is tapered to the diameter of the insulated conductor at a point along the catheter axis that coincides with the junction between the electrode and the insulated conductor. In another embodiment, the sheath is tapered to the diameter of the insulated conductor at a point along the catheter axis spaced in a proximal direction from the electrode.

In a preferred embodiment, the insulated conductor includes a semi-rigid conductor connected to the electrode and having sufficient length to provide mechanical support for the electrode, and a flexible conductor connected between the semi-rigid conductor and the proximal end of the catheter lead. The flexible sheath can be a tube or can be a coating on the insulated conductor.

The electroshock ablation catheter of the invention is typically utilized for electroshock ablation of tissue in the heart. In this case, the catheter has a size and flexibility that permits it to be advanced through a blood vessel to the heart. The electroshock ablation catheter is preferably utilized in conjunction with a surface electrode positioned on the skin of the patient. The catheter can include one or more proximal sensing electrodes that are utilized for mapping potentials within the heart.

The contoured electrode of the present invention permits the voltage, current and energy delivered through the catheter to be substantially increased in comparison with prior art electrodes without arcing. As a result, electroshock ablation of tissue within the heart can be performed more efficiently, with a reduced risk of undesired damage.

BRIEF DESCRIPTION OF THE DRAWINGS

For a better understanding of the present invention together with other and further objects, advantages and capabilities thereof, reference is made to the accompanying drawings which are incorporated herein by reference and in which.

DETAILED DESCRIPTION OF THE INVENTION

Figures 1, 2:
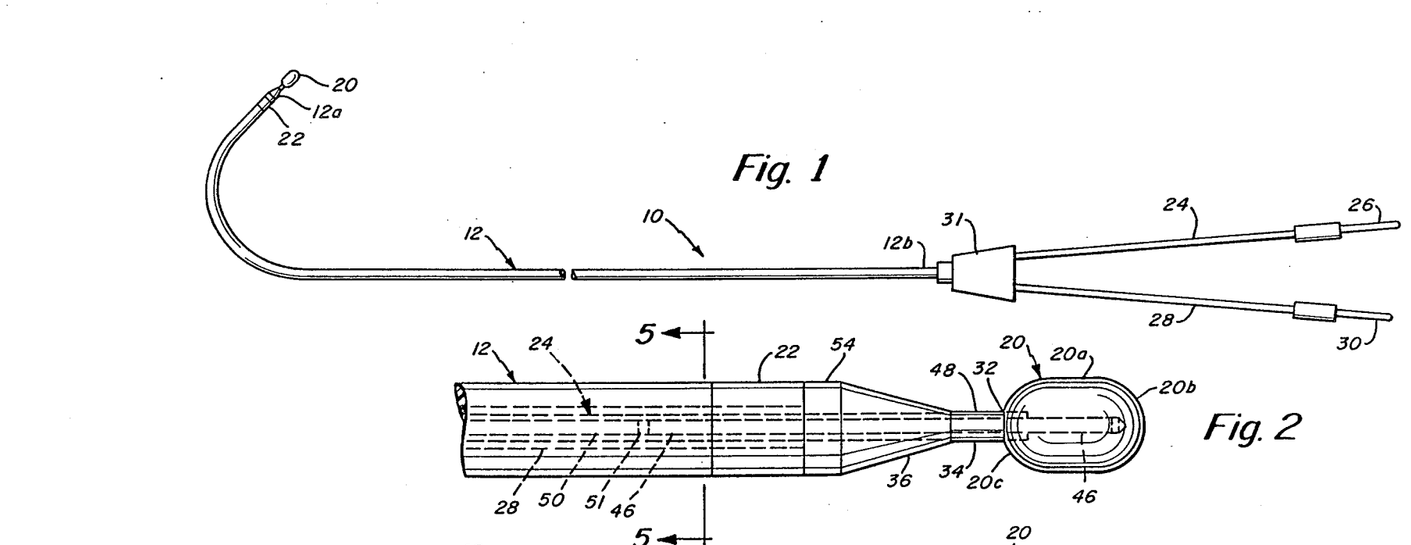
FIG. 1 is an elevation view of a catheter in accordance with the present invention.
FIG. 2 is an enlarged view of the distal end of the catheter of FIG. 1.

An electroshock ablation catheter 10 in accordance with the present invention is shown in FIG. 1. An elongated thin, flexible catheter lead 12 has a distal end 12a and a proximal end 12b. A contoured electroshock ablation electrode 20 is attached to the distal end 12a of catheter lead 12, and a proximal sensing electrode 22, typically used for mapping potentials within the heart, is proximally spaced from the electrode 20. The electrode 20 is electrically connected by means of an insulated electrical lead 24 extending through catheter lead 12 to a connector 26. The proximal electrode 22 is electrically connected by means of an electrical lead 28 extending through the catheter lead 12 to a connector 30. A bifurcation 31 separates the electrical leads 24 and 28 that extend through catheter lead 12. In use, the connector 26 is attached to an output terminal of an electrical energy source (not shown). A portion of the catheter lead 12 near the distal end thereof is formed into a prescribed shape known as a Damato curve. Other shapes can be utilized when appropriate.

An enlarged view of the distal portion of catheter 10 is shown in FIG. 2. In accordance with the present invention, the electrode 20 is contoured to provide a high arcing threshold. The arcing threshold is the voltage and/or current applied to electrode 20 at which arcing begins to occur. Thus, for applied voltages and currents lower than the arcing threshold, arcing does not occur. The contoured electrode of the invention provides an increased arcing threshold in comparison with prior art electrodes that were used for electroshock ablation. In accordanace with the present invention, the electrode 20 has a smoothly curved surface free of sharp edges. The electric field in the region of the electrode is relatively uniform, and high field concentrations that cause arcing are eliminated. In an important feature of the invention, the catheter lead 12 at the junction with electrode 20 has a smaller diameter than electrode 20. The electrode 20 surface curves inwardly at its proximal end to meet the catheter lead 12. This configuration further reduces the tendency for arcing.

In a preferred embodiment, the smoothly curved surface of electrode 20 includes a cylindrical surface 20a, a hemispherical distal end surface 20b and a hemispherical proximal end surface 20c. The surfaces 20a, 20b and 20c all have the same radius, thereby providing a smoothly curved outer surface. The preferred embodiment can thus be viewed as an elongated sphere.

Electrode 20 is attached to catheter lead 12 at a junction 32 which is carefully designed to insure a high arcing threshold. The diameter of catheter lead 12 at the junction 32 is smaller than the diameter of the electrode 20 in a plane perpendicular to the catheter axis. Preferably, the ratio between the diameter of electrode 20 and the diameter of catheter lead 12 at junction 32 is at least 3:1. When the electrode 20 includes cylindrical surface 20a, the diameter of electrode 20 is the diameter of cylindrical surface 20a.

In a preferred embodiment, the contoured electrode 20 and the catheter lead 12 are interconnected by a reduced diameter segment 34 and a tapered segment 36. The tapered segment 36 is a dielectric sheath, as described hereinafter. The reduced diameter segment 34 is an insulated conductor that is attached to the proximal end of contoured electrode 20. The diameter of segment 34 is no more than one-third of the diameter of cylindrical surface 20a. The tapered segment 36 is connected to the proximal end of segment 34 and provides a transition between segment 34 and catheter lead 12.

Figure 3:
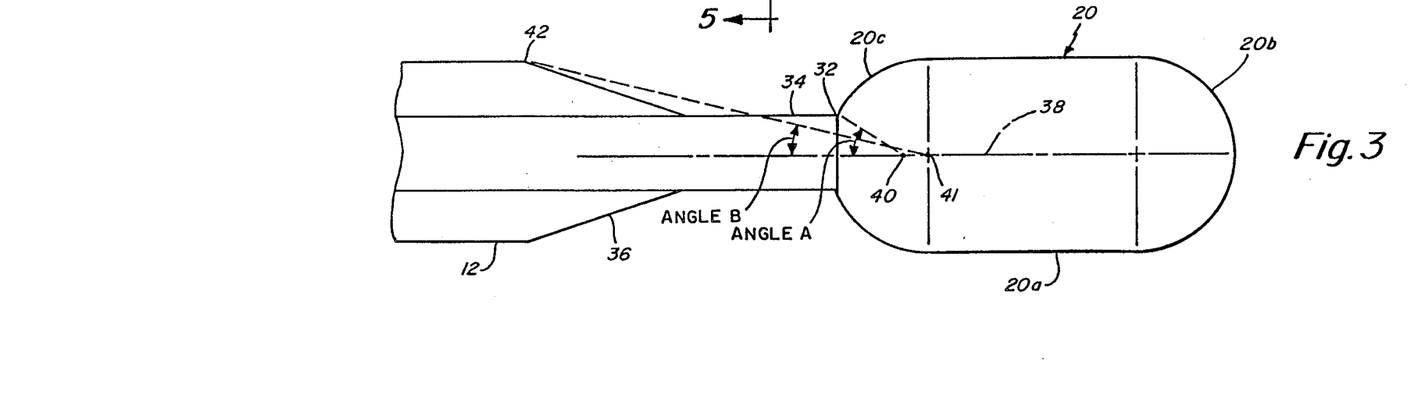
FIG. 3 is a schematic diagram that illustrates the design of the electrode and catheter lead.

A further requirement of the catheter configuration is illustrated in FIG. 3. The electrode 20 and the catheter lead 12 have a common central axis 38. An angle A is defined as the angle between the central axis 38 and a line drawn between the center of curvature 40 of proximal end surface 20c and the junction 32. An angle B is defined as the angle between the central axis 38 and a line drawn between a point 41 and a point 42. Point 41 is the point where a plane through the proximal end of cylindrical section 20a of the contoured electrode 20 intersects the central axis 38. Point 42 is the point at which the tapered segment 36 reaches full diameter. In the case where surface 20c is hemispherical, center of curvature 40 and point 41 coincide. In other cases, center of curvature 40 and point 41 are separated by a short distance. The electrode 20, the segment 34 and the tapered segment 36 should be configured such that the angle A is made as near as possible to zero by reducing the diameter of segment 34. However, the angle A should not be less than angle B. This requirement insures that a normal to the surface of electrode 20 at junction 32 does not pass through catheter lead 12.

The cylindrical surface 20a on electrode 20 permits delivery of higher current than a spherical electrode of equal diameter, since the surface area of the cylindrical surface 20a is greater and provides a high arcing threshold. The length of the cylindrical surface 20a is a compromise between the requirement for high current delivery and the requirements to perform ablation of a small area and to perform localized mapping. The diameter of the cylindrical portion 20a is preferably approximately the same as the diameter of the major portion of catheter lead 12. A smaller diameter would reduce the current that can be delivered with electrode 20, while a diameter larger than catheter lead 12 would cause potential difficulty in advancing the catheter 10 through a blood vessel to the heart.

In conventional pacing electrodes previously used for electroshock ablation, the electrode and the catheter lead had a uniform diameter throughout their length. In particular, the junction between the catheter lead and the electrode was the same diameter as the cylindrical electrode. In the conventional electrode, there is a steep electric field gradient at the junction of the insulation and the conductor and a rapid decrease away from the junction. The high electric field gradient produces a region where arcing is likely. In the ablation electrode of the present invention, the field gradient is smoothed out as a result of the electrode shape, and the field gradient is highly uniform across its surface. As a result, the tendency for arcing is reduced at given voltage and current levels.

Figure 4:
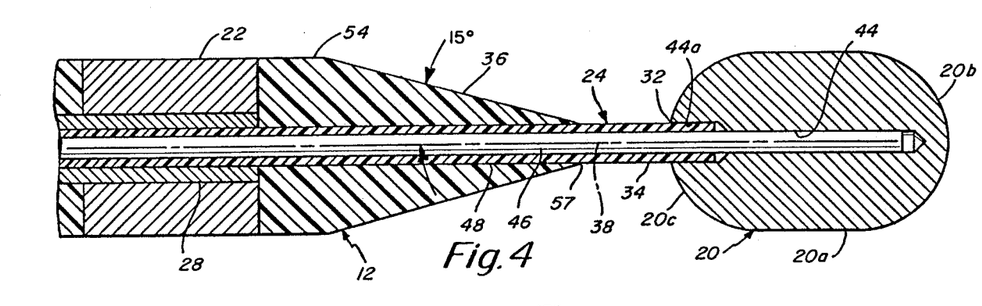
FIG. 4 is an enlarged cross-sectional view of the distal end of the catheter of FIG. 1.
Figure 5:
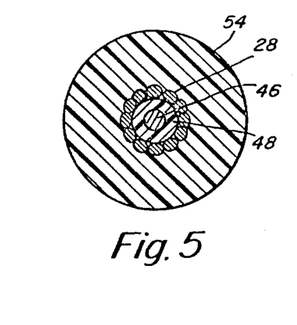
FIG. 5 is an enlarged cross-sectional view of the catheter lead taken along the line 5–5 of FIG. 2.

The detailed construction of a preferred embodiment of catheter 10 is shown in FIGS. 2, 4 and 5. The electrode 20 includes a bore 44 for attachment of catheter lead 12. The bore 44 is centered on proximal end surface 20c and is coaxial with cylindrical surface 20a. Preferably, catheter lead 12, cylindrical surface 20a and bore 44 have the common central axis 38. The insulated electrical lead 24 of catheter lead 12 includes a semi-rigid conductor 46 enclosed by an insulator 48. Conductor 46 extends into bore 44, and bore 44 includes a counterbore 44a that permits insulator 48 to extend into electrode 20. Semi-rigid conductor 46, which typically has a length of about one centimeter, extends from electrode 20 to a point along axis 38 spaced in a proximal direction from sensing electrode 22. The insulated electrical lead 24 further includes a flexible, stranded conductor 50 (FIG. 2) attached by a weld 51 to semi-rigid conductor 46. Conductor 50 extends through the remainder of catheter lead 12 to connector 26. The insulator 48 encloses conductors 46 and 50 and extends through catheter lead 12 to connector 26. The insulator 48 should be a high voltage dielectric material selected to withstand the maximum voltage to be applied to the catheter. The semi-rigid conductor 46 provides mechanical support for electrode 20 that would otherwise be lacking in a stranded, flexible conductor.

The proximal sensing electrode 22 is attached to electrical lead 28 which extends through catheter lead 12 to connector 30. In a preferred embodiment, the electrical lead 28 is a coaxial braid which surrounds insulator 48 as shown in FIG. 4. The coaxial braid is attached to sensing electrode 22 by means of a sleeve in a conventional manner.

The electrical lead 28 is enclosed by an insulating, flexible sheath 54. The flexible sheath 54 includes the tapered region 36. In the tapered region 36, the sheath 54 tapers from full diameter to the outside diameter of insulator 48. In a preferred embodiment, the surface of the sheath 54 is tapered in region 36 at an angle of about 15 degrees relative to axis 38. The tapered region 36, in a preferred embodiment, terminates at a point 57 along axis 38 that is spaced a short distance back from electrode 20. In another embodiment described hereinafter, the tapered region terminates at the junction of the electrode 20 and catheter lead 12.

The electrode 20 is preferably fabricated in 6-French (1.98 millimeters diameter) and 7-French (2.31 millimeters diameter) sizes, although other sizes could be used without departing from the scope of the invention. In an example of electrode 20, a 7-French electrode had an overall length of 4.7 millimeters. The semi-rigid conductor 46 had a diameter of 0.356 millimeter and the insulator 48 had a thickness of 0.152 millimeter, so that the outside diameter of electrical lead 24 was 0.660 millimeter. The region 36 of sheath 54 was tapered at an angle of about 15 degrees relative to axis 44, and sheath 54 terminated approximately one millimeter from electrode 20.

The electrode 20 is fabricated from a biocompatible metal such as platinum, and is typically machined from a rod of the desired material. The electrode 20 is mechanically and electrically connected to the semi-rigid conductor 46 by swaging, using a fixture with semicircular jaws. The connection can also be made by soldering, brazing or welding. The semi-rigid conductor 46 is attached to the stranded conductor 50 by welding. Brazing or soldering can also be used for this connection. The insulator 48 can be any dielectric material of sufficient dielectric strength and thickness to withstand the voltages commonly applied during electroshock ablation. In a preferred embodiment, the insulator 48 is Teflon.

The proximal sensing electrode 22, in a preferred embodiment, was spaced about four millimeters from electrode 20. The spacing depends on the intended use of the electrode. The proximal electrode 22 was fabricated of platinum and had a ring shape with a diameter equal to that of electrode 20 and a length of two millimeters. The proximal electrode 22 was connected to electrical lead 28 by swaging, although welding or soldering could be used.

The outer sheath 54 has a diameter the same as electrodes 20 and 22, except in the tapered region 36. The sheath 54 is a dielectric material with sufficient dielectric strength to withstand the voltages applied to electrode 20. The surface of the sheath 54 is coated with a material, such as a cross-linked, polyester-based polyurethane, that is non-thrombogenic. The wall of the sheath 54 can contain a radiopaque agent to assist in location during use. The sheath 54 can be woven dacron base with a coating of crosslinked polymers. However, the sheath 54 is not limited to such a construction.

In the embodiment described above, the catheter lead 12 is a composite construction; that is, the conductors 46, 50, insulator 48, electrical lead 28 and sheath 54 are formed as an integral catheter lead assembly. Sheath 54 is formed as a coating on electrical lead 24. In an alternative construction, the conductors 46 and 50, insulator 48 and electrical lead 28 can be fabricated as an assembly which is inserted through a lumen of a flexible tube. the flexible tube is tapered in a region near the electrode 20 as described above in connection with sheath 54. It will be understood that proximal electrode 22 is not a necessary component of the electroshock ablation catheter of the present invention. In some cases, the proximal electrode is omitted, while in the other cases, two or more proximal electrodes may be utilized.

Figure 6:
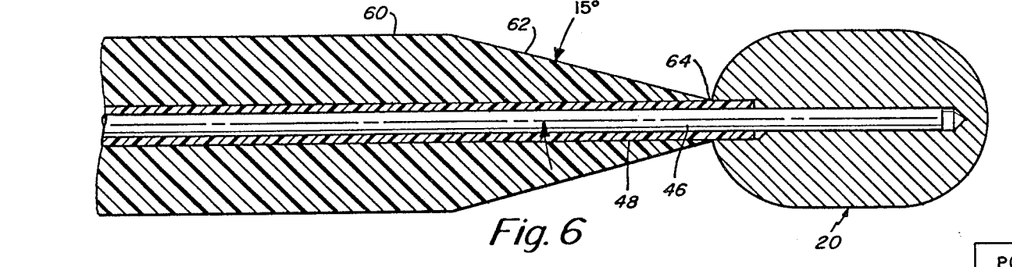
FIG. 6 is an enlarged cross-sectional view of the distal end of a catheter in accordance with another embodiment of the present invention.

An alternate embodiment of the catheter in accordance with the present is shown in FIG. 6. The electrode 20, the semi-rigid conductor 46 and insulator 48 are the same as shown in FIGS. 2, 4 and 5 and described hereinabove. The proximal electrode is omitted in the embodiment of FIG. 6. A flexible insulating sheath 60, having the same diameter as electrode 20, surrounds insulator 48 and semi-rigid conductor 46. The flexible sheath 60 extends to the proximal end of the catheter lead. As in the embodiment of FIGS. 2, 4 and 5, the semi-rigid conductor 46 is coupled to a flexible stranded conductor (not shown) approximately one centimeter back from electrode 20. The sheath 60 includes a tapered region 62 wherein the sheath 60 is tapered from full diameter to a diameter equal to the outside diameter of insulator 48. The tapered region 62 terminates at the junction 64 of electrode 20 and the catheter lead. The angle of the taper, preferably about 15 degrees, is approximately equal to the angle between a normal to the surface of electrode 20 where the semi-rigid conductor 46 and insulator 48 intersect electrode 20, and the catheter axis. This configuration meets the requirement that the concentration of electric field lines be minimized and that a line perpendicular to the surface of electrode 20 not intersect the catheter lead.

Figure 7:
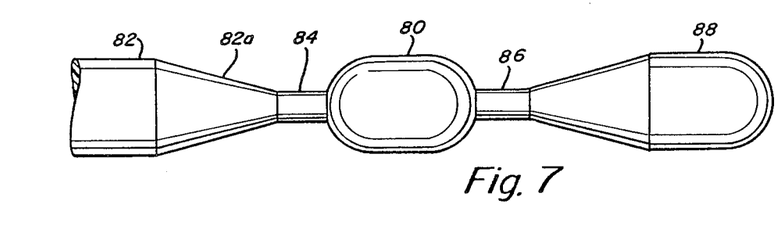
FIG. 7 is an enlarged view of the distal end of a catheter in accordance with yet another embodiment of the present invention.

Another catheter construction utilizing the contoured ablation electrode of the present invention is illustrated in FIG. 7. A contoured electrode 80 is connected to a catheter lead 82. The electrode 80 has a smoothly-curved surface, preferably including a cylindrical surface and hemispherical end surfaces. An insulated electrical lead 84 of smaller diameter than electrode 80 interconnects electrode 80 and catheter lead 82. The catheter lead 82 includes a tapered portion 82a and is similar in construction to the embodiment of FIG. 4. The embodiment of FIG. 7 differs from the embodiments described hereinabove in that the electrode 80 is not located at the distal end of the catheter. A semi-rigid rod 86 extending from the distal end of electrode 80 connects an insulating element 88 to electrode 80. The rod 86 is smaller in diameter than electrode 80 and is either a solid insulator or an insulated conductor. The embodiment of FIG. 7 provides a contoured ablation electrode that is spaced back from the distal end of the catheter. It will be understood that more than one contoured ablation electrode can be utilized on a single catheter. For example, the insulating element 88 can be replaced with a second contoured electrode, if desired. The location of the contoured electrode on the catheter depends on the physical characteristics of the organ being treated and the parameters of the ablation process.

In use, the catheter in accordance with the present invention is advanced through an artery or a vein to the desired location within the heart. An external, large surface area electrode (not shown) is attached to the skin of the patient on the back or the chest, depending on the desired direction of ablation. The potentials within the heart can be mapped using electrodes 20 and 22 as sensing electrodes. The preformed, curved shape at the distal end of the catheter assists in reaching specific locations in the heart. After the heart has been satisfactorily mapped and the target site for ablation has been identified, the electrode 20 is positioned at the desired site and is energized with a high voltage source capable of providing the desired electroshock ablation waveform. One or more high energy pulses are supplied from the source through the catheter lead 12 to electrode 20 until the desired electroshock ablation is accomplished. The applied pulse is typically in the range of 2.0–2.5 kilovolts peak and has a duration in the range of about 2–10 milliseconds. Typically, the applied pulse has a rapid rise time and an exponential decay. It will be understood that these values are given by way of example and that other voltages, pulse durations and waveshapes can be utilized. Furthermore, although the ablation electrode of the present invention is intended primarily for use in the heart, it is not limited to such use.

As noted above, an object of the present invention is to provide an electroshock ablation electrode having a higher arcing threshold than prior art electrodes. Comparative tests of arcing thresholds were performed on conventional pacing electrodes in accordance with the prior art and a contoured ablation electrode in accordance with the present invention. The conventional electrode was a 7F pacing electrode having a hemispherical distal end. The electrode of the present invention (new electrode) was a 7F contoured electrode constructed as shown in FIGS. 2, 4 and 5 and described hereinabove. The arcing thresholds were measured using the conventional electrode and the new electrode as both the cathode and the anode of the shock. Energy was delivered using both conventional inductancemodified, high energy shocks (Lown defibrillator) and also short-time constant capacitive discharges (NHH ablater). The Lown defibrillator produces a damped, sinusoidal waveform, while the NHH ablater produces a pulse having a rapid rise time and an exponential decay.

Figure 8:
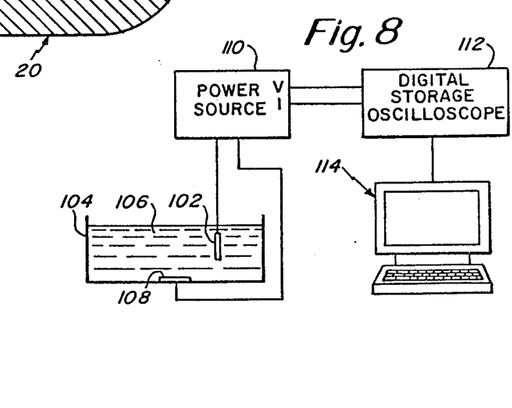
FIG. 8 is a schematic diagram of an arrangement for measuring arcing thresholds of electroshock ablation catheters.

The test setup for measurement of arcing thresholds is shown in FIG. 8. A test electrode 102 was suspended in a tank 104 of physiological saline 106. A large area indifferent electrode 108 was positioned in the bottom of the tank 104. High energy shocks were delivered to the electrode 102 from a power source (Lown defibrillator or NHH ablater) 110 and the occurrence of arcing was estimated visually and by observation of disturbances in the delivered voltage and current curves. The voltage and current curves were stored on a digital storage oscilloscope 112 and were transferred to a microcomputer 114 for accurate estimation of delivered energy.

Figure 9A:
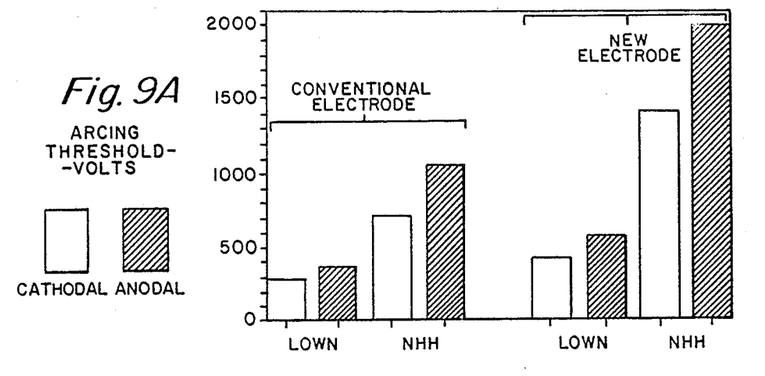
FIGS. 9A–9C are graphic representations of arcing threshold test results for prior art conventional electrodes and contoured electrodes in accordance with the present invention.
Figure 9B:
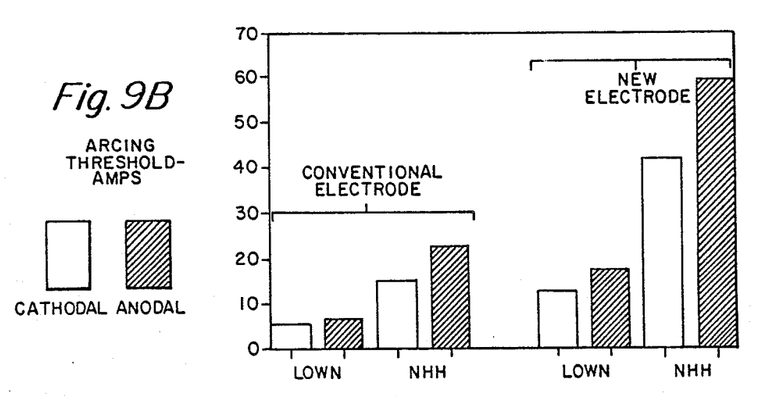
Figure 9C:
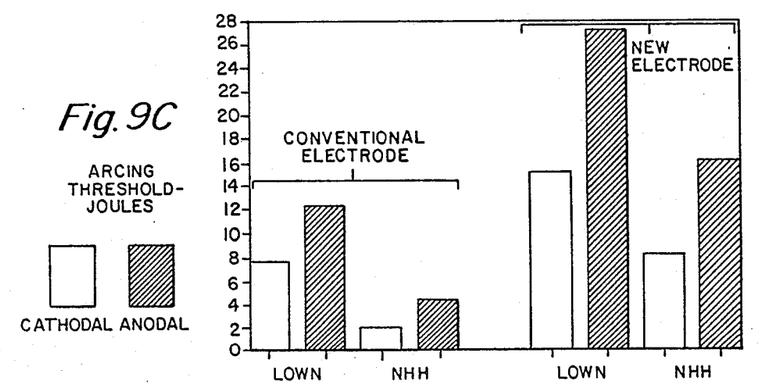

The results of the measurements are illustrated in FIGS. 9A-9C. The arcing thresholds in volts for the conventional electrode and the new electrode are shown in FIG. 9A. The arcing current thresholds in amps for the conventional electrode and the new electrode are shown in FIG. 9B. The arcing thresholds in joules are shown in FIG. 9C. In all combinations, the contoured ablation electrode of the present invention gave superior arcing threshold performance in comparison with the conventional electrode. The mean increases in peak voltage, peak current and delivered energy at arcing threshold were 74%, 157% and 188%, respectively.

While there has been shown and described what is at present considered the preferred embodiments of the present invention, it will be obvious to those skilled in the art that various changes and modifications may be made therein without departing from the scope of the invention as defined by the appended claims.

What is claimed is:

1. A catheter which can be advanced through a body vessel to an internal organ for high voltage electroshock ablation of a desired portion of the internal organ without arcing, said catheter comprising:
   an electrode for conducting electrical energy to the desired portion of the internal organ, said electrode having a smoothly curved surface free of sharp edges;
   an elongated conductor coupled to said electrode, said conductor having a proximal end for coupling to an external source of electrical energy;
   electrical insulation surrounding said elongated conductor, said conductor and said insulation defining an electrical lead having a central axis, said electrical lead having suitable diameter and flexibility to be advanced through the body vessel to the internal organ, said electrical lead having a cross-sectional dimension at the junction with said electrode that is less than the maximum cross-sectional dimension of said electrode; and
   a flexible, insulating sheath surrounding a major portion of said electrical lead, said insulating sheath having a diameter approximately equal to the maximum cross-sectional dimension of said electrode, said insulating sheath being tapered from full diameter at a first point on said central axis to the diameter of said electrical lead at a second point on said central axis adjacent to said electrode.

2. A catheter as defined in claim 1 wherein said smoothly curved surface includes a cylindrical surface coaxial with said central axis and a proximal end surface joining said cylindrical surface to said electrical lead.

3. A catheter as defined in claim 2 wherein said proximal end surface has a hemispherical shape.

4. A catheter as defined in claim 2 wherein the diameter of said electrical lead at the junction with said electrode is no greater than one-third of the diameter of said cylindrical surface.

5. A catheter as defined in claim 2 wherein said smoothly curved surface further includes a distal end surface having a hemispherical shape.

6. A catheter as defined in claim 5 wherein said electrode includes an opening in said proximal end surface and wherein said conductor and said insulation extend into said opening.

7. A catheter as defined in claim 1 wherein said elongated conductor includes a semi-rigid conductor connected to said electrode and having sufficient length to provide mechanical support for said electrode, and a flexible conductor connected between said semi-rigid conductor and the proximal end of said elongated conductor.

8. A catheter as defined in claim 1 wherein the ratio of the maximum cross-sectional dimension of said electrode to the cross sectional dimension of said electrical lead at the junction with said electrode is at least 3:1.

9. A catheter as defined in claim 1 wherein said second point coincides with the junction between said electrode and said electrical lead.

10. A catheter as defined in claim 1 wherein said second point is spaced in a proximal direction from the junction between said electrode and said electrical lead.

11. A catheter as defined in claim 1 wherein said second point being located between 0.0 and 1.0 millimeter from the junction between said electrode and said electrical lead.

12. A catheter as defined in claim 11 wherein said sheath is tapered at an angle of about 15 degrees with respect to said central axis.

13. A catheter as defined in claim 1 wherein said smoothly curved surface includes a cylindrical surface coaxial with said central axis and a hemispherical proximal end surface joining said cylindrical surface to said electrical lead, said cylindrical surface and said hemispherical end surface having the same diameter.

14. A catheter as defined in claim 13 wherein a line drawn through the center of curvature of said hemispherical proximal end surface and the junction of said electrical lead with said electrode does not pass though said insulating sheath.

15. A catheter as defined in claim 1 further including a proximal electrode located on said insulating sheath.

16. A catheter which can be advanced through a blood vessel to the heart for high voltage electroshock ablation of tissue in the heart without arcing, said catheter comprising:
   an electrode for conducting electrical energy to the desired tissue in the heart, said electrode having a smoothly curved surface free of sharp edges; and
   a catheter lead having suitable diameter and flexibility to be advanced through the blood vessel to the heart, said catheter lead including an elongated conductor coupled to said electrode, said elongated conductor having a proximal end for coupling to an external source of electrical energy, said conductor being surrounded by electrical insulation, said smoothly curved surface of said electrode including a cylindrical surface coaxial with said catheter lead and a proximal end surface joining said cylindrical surface to said catheter lead, said catheter lead having a cross-sectional dimension at the junction with said electrode that is less then the diameter of said cylindrical surface, the ratio of the diameter of said cylindrical surface to the cross-sectional dimension of said catheter lead at the junction with said electrode being at least 3:1.

17. A catheter as defined in claim 16 wherein said smoothly curved surface further includes a distal end surface having a hemispherical shape.

18. A catheter as defined in claim 16 wherein said electrode includes an opening in said proximal end surface and wherein said conductor and said insulation extend into said opening.

19. A catheter as defined in claim 16 wherein said elongated conductor includes a semi-rigid conductor connected to said electrode and having sufficient length to provide mechanical support for said electrode, and a flexible conductor connected between said semi-rigid conductor and the proximal end of said elongated conductor.

20. A catheter which can be advanced through a blood vessel to the heart for high voltage electroshock ablation of tissue in the heart wihout arcing, said catheter comprising:
an electrode for conducting electrical energy to the desired tissue in the heart, said electrode having a smoothly curved surface free of sharp edges; and
a catheter lead having a central axis and having suitable diameter and flexibility to be advanced through the blood vessel to the heart, said catheter lead including
an elongated, thin flexible insulating sheath having a distal end and a proximal end, and
an insulated conductor extending through said flexible sheath and being coupled to said electrode, said conductor having a proximal end for coupling to an external source of electrical energy, said smoothly curved surface of said electrode including a cylindrical surface coaxial with said catheter lead and a proximal end surface joining said cylindrical surface to said insulated conductor, said insulated conductor having a diameter at the junction with said electrode that is less than the diameter of said cylindrical surface, said flexible sheath and the cylindrical surface of said electrode having approximately the same diameter, said insulating sheath being tapered from full diameter at a first point on said central axis to the diameter of said insulated conductor at a second point on said central axis adjacent to said electrode.

21. A catheter as defined in claim 20 wherein said electrode includes an opening in said proximal end surface and wherein said insulated conductor extends into said opening.

22. A catheter as defined in claim 20 wherein said insulated conductor includes a semi-rigid conductor connected to said electrode and having sufficient length to provide mechanical support for said electrode, and a flexible conductor connected between said semi-rigid conductor and the proximal end of said insulated conductor.

23. A catheter as defined in claim 20 wherein said second point coincides with the junction between said electrode and said insulated conductor.

24. A catheter as defined in claim 20 wherein said second point is spaced in a proximal direction from the junction between said electrode and said insulated conductor.

25. A catheter as defined in claim 20 wherein said second point being located between 0.0 and 1.0 millimeter from the junction between said electrode and said insulated conductor.

26. A catheter as defined in claim 25 wherein said sheath is tapered at an angle of about 15 degrees with respect to said central axis.

27. A catheter as defined in claim 20 wherein said proximal end surface has a hemispherical shape and wherein a line drawn through the center of curvature of said hemispherical proximal end surface and the junction of said insulated conductor with said electrode does not pass though said insulating sheath.

28. A catheter as defined in claim 20 further including a proximal electrode located on said catheter lead and spaced proximally from said electrode, and a proximal electrode conductor coupled to said proximal electrode and extending through said flexible sheath to the proximal end thereof.

29. A catheter as defined in claim 20 wherein said proximal end surface has a hemispherical shape.

30. A catheter as defined in claim 20 wherein the ratio of the diameter of said cylindrical surface to the cross-sectional dimension of said catheter lead at the junction with said electrode is at least 3:1.

31. A catheter which can be advanced through a body vessel to an internal organ for electroshock ablation of a desired portion of the internal organ, said catheter comprising:
an electrode for conducting electrical energy to the desired portion of the internal organ, said electrode having a smoothly curved surface free of sharp edges;
an elongated conductor coupled to said electrode, said electrode having a proximal end for coupling to an external source of electrical energy; and
electrical insulation surrounding said elongated conductor, said conductor and said insulation defining an electrical lead having a central axis, said electrical lead having a suitable diameter and flexibility to be advanced through the body vessel to the internal organ, said electrical lead having a cross-sectional dimension at the junction with said electrode that is less than a maximum cross-sectional dimension of said electrode, wherein the ratio of the maximum cross-sectional dimension of said electrode to the cross-sectional dimension of said electrical lead at the junction with said electrode is at least 3:1.

32. A catheter which can be advanced through a blood vessel to the heart for electroshock ablation of tissue in the heart, said catheter comprising:
an electrode for conducting electrical energy to the desired tissue in the heart, said electrode having a smoothly curved surface free of sharp edges; and
a catheter lead having suitable diameter and flexibility to be advanced through the blood vessel to the heart, said catheter lead including an elongated conductor coupled to said electrode, said elongated conductor having a proximal end for coupling to an external source of electrical energy, said conductor being surrounded by electrical insulation, said smoothly curved surface of said electrode including a cylindrical surface coaxial with said catheter lead and a proximal end surface joining said cylindrical surface to said catheter lead, said catheter lead having a cross-sectional dimension at the junction with said electrode that is less than the diameter of said cylindrical surface, said catheter lead and said cylindrical surface having approximately the same diameter, said catheter lead being tapered from full diameter at a first point on said central axis to no greater than one third full diameter at a second point on said central axis adjacent to said electrode.

33. A catheter as defined in claim 32 wherein said proximal end surface has a hemispherical shape and wherein said smoothly curved surface further includes a distal end surface having a hemispherical shape, said proximal and said distal end surfaces having the same diameter as said cylindrical surface.

34. A catheter which can be advanced through a body vessel to an internal organ for electroshock ablation of a desired portion of the internal organ, said catheter comprising:
    an electrode for conducting electrical energy to the desired portion of the internal organ, said electrode having a smoothly curved surface free of sharp edges;
    an elongated conductor coupled to said electrode; said conductor having a proximal end for coupling to an external source of electrical energy;
    electrical insulation surrounding said elongated conductor, said conductor and said insulation defining an electrical lead having a central axis, said electrical lead having suitable diameter and flexibility to be advanced through the body vessel to the internal organ, said electrical lead having a cross-sectional dimension at the junction with said electrode that is less than a maximum cross-sectional dimension of said electrode; and
    a flexible, insulating sheath surrounding a major portion of said electrical lead, wherein said sheath is tapered from full diameter at a first point on said central axis to the diameter of said electrical lead at a second point on said central axis, said second point being located between 0.0 and 1.0 millimeter from the junction between said electrode and said electrical lead.

35. A catheter which can be advanced through a blood vessel to the heart for electroshock ablation of tissue in the heart, said catheter comprising:
    an electrode for conducting electrical energy to the desired tissue in the heart, said electrode having a smoothly curved surface free of sharp edges; and
    a catheter lead having a central axis and having suitable diameter and flexibility to be advanced through the blood vessel to the heart, said catheter lead including
    an elongated, thin, flexible insulating sheath having a distal end and a proximal end, and
    an insulated conductor extending through said flexible sheath and being coupled to said electrode, said conductor having a proximal end for coupling to an external source of electrical energy, said smoothly curved surface of said electrode including a cylindrical surface coaxial with said catheter lead and a proximal end surface joining said cylindrical surface to said insulated conductor, said insulated conductor having a diameter at the junction with said electrode that is less than the diameter of said cylindrical surface, wherein said sheath is tapered from full diameter at a first point on central axis to the diameter of said insulated conductor at a second point on said on central axis, said second point being located between 0.0 and 1.0 millimeter from the junction between said electrode and insulated conductor.

* * * * *